United States Patent [19]

Granwehr et al.

[11] 4,229,367
[45] Oct. 21, 1980

[54] PREPARATION OF TRANS-4-ALKYL-CYANOARYLCYCLOHEXANES

[75] Inventors: Bernhard Granwehr, Zofingen; René Gnehm, Küngoldingen, both of Switzerland

[73] Assignee: Siegfried Aktiengesellschaft, Switzerland

[21] Appl. No.: 39,134

[22] Filed: May 15, 1979

[30] Foreign Application Priority Data

May 23, 1978 [DE] Fed. Rep. of Germany ....... 2822504

[51] Int. Cl.$^3$ ............................................ C07C 121/64
[52] U.S. Cl. ............................... 260/465 R; 252/299; 260/544 P; 260/558 R; 560/102; 562/492
[58] Field of Search ...................... 260/465 R; 560/102

[56] References Cited

U.S. PATENT DOCUMENTS

| | | | |
|---|---|---|---|
| 3,852,286 | 12/1974 | Hall et al. | 560/102 X |
| 4,016,204 | 4/1977 | Rajadhyaksha | 560/102 X |
| 4,130,502 | 12/1978 | Eidenschink et al. | 252/299 |

FOREIGN PATENT DOCUMENTS 2701591  7/1978  Fed. Rep. of Germany .

*Primary Examiner*—Dolph H. Torrence
*Attorney, Agent, or Firm*—Burns, Doane, Swecker & Mathis

[57] ABSTRACT

Trans-4-alkyl-cyanoarylcyclohexanes are prepared in a stereoselective manner from arylcarboxylic acids of the formula Ar-[Ar]$_n$-Ar-4-COOH, Ar being aryl and n being 0 to 2, by first converting such a carboxylic acid to a mixture of the cis and trans isomers of the corresponding cyclohexa-2,5-diene-4-carboxylic acid, esterifying the resulting isomer mixture with a lower alkanol and further hydrogenating the resulting esters/isomers to produce the cis and trans isomers of the corresponding cyclohexane-4-carboxylic acid esters, isomerizing the cis isomers in the mixture to the trans isomer thereby producing a mixture containing the trans isomer substantially free from cis isomer, stereospecifically saponifying the trans isomer, growing a carbon chain of desired length on the carboxyl group of the resulting carboxylic acid, reducing the carbonyl group thereof, and introducing a cyano group into the terminal aryl group. The resulting product is useful as a nematic liquid crystal.

10 Claims, No Drawings

PREPARATION OF TRANS-4-ALKYL-CYANOARYLCYCLOHEXANES

DESCRIPTION

Introduction

The invention relates to a process for the stereoselective preparation of trans-4-alkyl-cyanoarylcyclohexanes of the formula:

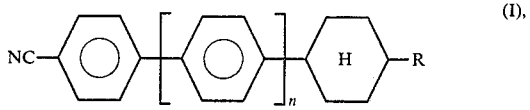

in which R is an unbranched or singly branched aliphatic hydrocarbon radical of 1 to 12 carbon atoms and n is an integer in the range from 0 to 2.

The trans-4-alkyl-cyanoarylcyclohexanes corresponding to Formula (I) are capable of forming nematic liquid crystal phases. They are preferably used as components of liquid crystal mixtures, especially nematic liquid crystal mixtures.

The trans-4-alkyl-(4'-cyanophenyl)cyclohexanes and the trans-4-alkyl-(4''-cyanobiphenyl-4'-yl)cyclohexanes are known compounds.

The trans-4-alkyl-(4'''-cyanoterphenyl-4'-yl)cyclohexanes are new substances. As components of liquid crystal mixtures they have the capability of enlarging the range of existence of the meso phase and of improving its stability without significantly increasing the switching times of these mixtures.

The 4-alkyl-cyanoarylcyclohexanes exist in a cis form and a trans form. Only the trans form is usable as a liquid crystal or a component of a liquid crystal mixture.

PRIOR ART

A process for preparing trans-4-alkyl-(4'-cyanophenyl)cyclohexanes is disclosed in Angew. Chem. 89, 103. 4-Alkylcyclohexanone is converted to a mixture of the two cis-trans isomers of 4-alkyl-1-phenyl-cyclohexanol with phenyl magnesium bromide in diethyl ether. The isomeric mixture is separated in a chromatographic column and separately recovered. The trans isomers are hydrogenated with molecular hydrogen in the presence of a Raney nickel catalyst, the cis isomers in the presence of palladium on activated carbon. When hydrogenating the cis isomer, isomerization to the trans isomer takes place. Both of the resulting trans-4-alkyl-phenyl-cyclohexane fractions are combined, acetylated according to Friedel-Crafts, subjected to haloform degradation to carboxylic acid, converted to the acid amide and finally dehydrated to the nitrile with POCl₃.

It is a disadvantage of this known process that the 4-alkylcyclohexanones are available only with difficulty, a chromatic separation of the difficultly separable cis-trans isomers of the cyclohexanols is required and the chromatographically separated isomers must then be separately hydrogenated.

OBJECTS

It is an object of this invention to provide a process for the stereoselective preparation of trans-4-alkyl-cyanoarylcyclohexanes of the kind described above, which is simple and economical. A more particular object is to provide such a process that is based on the use of readily accessible and relatively inexpensive starting materials and that does not require any separation and separate treatment of isomeric intermediates.

These and other objects as well as the nature and scope of this invention, will become apparent from the following description and appended claims.

GENERAL DESCRIPTION

The biphenyl-, terphenyl- or quaterphenyl-4-carboxylic acids that are required as starting materials in this process are commonly available in commerce. As is well known, the biphenyl-4-carboxylic acid is readily prepared from the corresponding 4-bromo derivative by the Grignard reaction while the higher polyphenyl carboxylic acids can be prepared, for instance, by conversion with organolithium as described by H. Gilman (J. Org. Chem. 22, 446).

According to the invention, the cyclohexane-4-carboxylic acid esters that are obtained as an isomeric mixture from the starting acid by hydrogenation and esterification with a lower alkanol, e.g., methanol, ethanol, isopropanol or tert-butanol, can be quantitatively isomerized to the stereochemically pure trans-arylcyclohexane-4-carboxylic acid alkyl ester, e.g., the ethyl ester, without requiring separation of the cis-trans isomers. This can be done by treatment of the ester mixture in an anhydrous alkanol, preferably in anhydrous ethanol, under an inert gas such as nitrogen or argon in the presence of sodium or potassium, preferably in the presence of about 10 mole percent sodium based on the esters to be treated. If in doing this a methyl ester mixture is isomerized instead of the ethyl ester mixture and absolute ethanol is used as the isomerization medium, a transesterification takes place such that the trans-ethyl ester is actually obtained because of the presence of absolute ethanol in this step.

The resulting trans-arylcyclohexane-4-carboxylic acid ethyl ester is readily saponifiable in an otherwise well-known manner. For instance, the saponification can be efficiently conducted by using lithium hydroxide monohydrate in ethanol solution, which is the preferred saponifying agent. However, other alkali metal and alkaline earth metal hydroxides in alcoholic solution can be used similarly.

The resulting trans-arylcyclohexane-4-carboxylic acid is subsequently subjected to chain growth in a conventional manner and the carbonyl group in the α-position is then reduced. The chain growth must be conducted at low temperatures, e.g., at below −20° C., preferably between −50° and −100° C., and most preferably at −70° C., in order to have it proceed stereospecifically. The reaction is conducted under absolutely anhydrous conditions, preferably in tetrahydrofuran and/or hexane. If the aromatic residue is a phenyl radical, one may perhalogenate, preferably percholorinate, the phenyl residue prior to the chain growth reaction, preferably prior to the saponification. The required dehalogenation can then take place either before or after reduction of the carbonyl group.

In selecting among the innumerable known processes for obtaining chain growth it is important to take heed that deprotonation of the cyclohexane in the 4-position is definitely precluded. The chain growth method using the reaction with alkyl lithium, which is preferred because of its good yields, proceeds quantitatively in a stereospecific manner. Suitable alkyl metal compounds include, for instance, methyl lithium, n-propyllithium, iso-propyllithium, n-butyllithium, n-undecyllithium and other similar unbranched or singly branched organic metal compounds containing 1 to 11 or 12 carbon atoms per alkyl group.

The subsequent reduction of the carbonyl group can be obtained in a well-known manner, for instance according to Clemmensen or Wolff-Kishner.

The trans-4-alkyl-arylcyclohexane obtained after such reduction corresponds to the trans-4-alkyl-phenyl-cyclohexane that is obtained as an intermediate product in the previously known process. The introduction of the cyano group can then take place the same way as has been done in the prior art, via acetylation and a haloform degradation with subsequent dehydration of the amide. It is preferable, however, to do so via the direct conversion of the trans-4-alkyl-arylcyclohexane in the presence of aluminum chloride with oxalyl chloride according to Friedel-Crafts, which surprisingly also proceeds quantitatively stereospecifically and with high yields. The obtained 4'-, 4"- or 4'"-acid chloride can then be converted to the nitrile in one step via the amide.

Naturally, instead of the cyano group in the p-position of the aryl residue one can introduce other groups as may be desired, especially ester groups. Likewise, instead of the chain growth and subsequent reduction of the carbonyl group in the 4-position of the cyclohexane one can perform other modifications, for instance an esterification or transesterification with an alcohol, as is otherwise well known and common in the art pertaining to the preparation of compositions for nematic liquid crystal phases.

PREFERRED EMBODIMENT

The invention is further illustrated by the following working example.

EXAMPLE

A total 6.0 g sodium, i.e., a source of solvated electrons, is added in small portions in the course of 60 minutes under nitrogen at −70° C. to 16.2 g (0.082 mol) of a commercially available biphenyl-4-carboxylic acid in 30 g absolute anhydrous ethanol, i.e., a proton donor, and 300 ml anhydrous ammonia (to provide solvated electrons). 50 g solid ammonium chloride and 70 ml cold water are added to the resulting suspension after completion of the reaction. Subsequently the ammonia is removed under reduced pressure. After dilution with an additional 30 to 50 ml water the mixture is extracted with 100 ml diethyl ether. Subsequently the mixture is acidified with concentrated hydrochloric acid and extracted three more times with ether. The combined ether phases are dried over magnesium sulfate and concentrated. In doing this 14.6 g of a white crystalline substance precipitates out that is identified as an isomeric mixture of cis- and trans-phenylcyclohexa-2,5-diene-4-carboxylic acid.

10 g (0.050 mol) of the obtained isomeric mixture is dissolved in 5 to 10 ml methanol and a catalytic amount of p-toluenesulfonic acid and 50 ml carbon tetrachloride are added. The mixture is heated for 10 hours under reflux at atmospheric pressure. After cooling and complete separation of the two phases the carbon tetrachloride phase is removed, concentrated and dissolved in anhydrous ethanol. Subsequently it is hydrogenated with hydrogen gas using a palladium/activated carbon catalyst. After consumption of the calculated amount of hydrogen the catalyst is removed by filtration. A few milliliters of benzene are added to the reaction mixture in order to remove even the last traces of water as an azeotrope. The thus dried reaction mixture is subsequently treated with 10 mole percent sodium under nitrogen and heated 48 hours under reflux at atmospheric pressure. Subsequently, the mixture is cooled, concentrated, mixed with water, neutralized and extracted several times with diethyl ether. The combined ether extracts are dried. The ether solvent is subsequently removed under reduced pressure. 10.5 g of practically pure, white trans-phenylcyclohexane-4-carboxylic ethyl ester is thus obtained.

10.0 g (0.043 mol) of the obtained stereochemically pure ester is dissolved in ethanol and 2.7 g (0.065 mol) lithium hydroxide monohydrate is added. After completion of the saponification the reaction mixture is neutralized with an ethanol solution of hydrochloric acid, concentrated, water is removed from it by azeotropic distillation upon addition of benzene and the product is suspended in tetrahydrofuran. The suspension is cooled to −70° C. and 0.043 mol n-butyllithium in hexane is added under nitrogen. The reaction mixture is stirred at this temperature for one hour. Thereafter the reaction mixture is removed from the cryostat and poured at room temperature into an ice/water mixture. The resulting mixture is neutralized, concentrated and taken up in dioxane. The obtained ketone is then directly reduced at room temperature without any prior isolation in the usual manner according to Clemmensen. After recrystallization 5.6 g of white trans-4-n-pentyl-phenylcyclohexane are obtained.

The cyano group can then be introduced into the 4'-position of the phenyl residue of the thus obtained substance according to the known technique described in Angew. Chem. 89, 103.

Alternatively, one can convert the obtained trans-4-n-pentylphenyl-cyclohexane in the presence of anhydrous aluminum chloride with oxalyl chloride to the corresponding 4'-acid chloride and subsequently convert it to the trans-4-n-pentyl-(4'-cyanophenyl)cyclohexane via the amide and by dehydration of the amide with $POCl_3$. The trans-4-n-pentyl-(4'-cyanophenyl)cyclohexane has a melting point of 30° to 30.5° C. and a clear point of 55° C. The resulting compound exhibits nematic behavior such that the presence of the equatorial trans-form is presumed.

What we claim is:

1. In a process for the preparation of a trans-4-alkyl-cyanoarylcyclohexane having the formula:

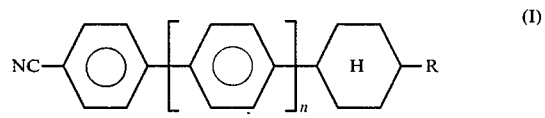

(I)

in which R is an unbranched or singly branched alkyl radical of 1 to 12 carbon atoms and n is an integer in the range from 0 to 2, from an arylcarboxylic acid of the formula

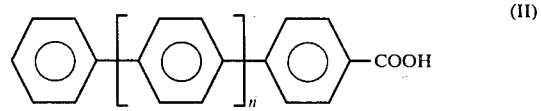

(II)

wherein n is the same as in Formula (I) above, in which process (a) an arylcarboxylic acid having the Formula (II) is hydrogenated to produce a mixture of both the corresponding cis and trans isomers of aryl substituted cyclohexa-2,5-diene-4-carboxylic acid having the formula:

(III);

[structure: Ar—[Ar]ₙ—cyclohexadiene—COOH]

wherein n is the same as in Formula (I) above, (b) the produced mixture of aryl substituted cyclohexadiene carboxylic acid isomers having the Formula (III) is esterified with a lower alkanol whereby a mixture of the corresponding carboxylic acid alkyl ester isomers is produced, (c) the resulting mixture of aryl susbstituted cyclohexadiene carboxylic acid alkyl ester isomers is hydrogenated whereby the corresponding cis and trans isomers of 1-aryl substituted cyclohexane-4-carboxylic acid alkyl ester are produced having the formula:

(IV);

[structure: Ar—[Ar]ₙ—cyclohexane(H)—COO-lower alkyl]

(d) the aryl substituted cyclohexane-4-carboxylic acid alkyl ester is saponified and the resulting salt is converted to the corresponding free carboxylic acid;

(e) the resulting free carboxylic acid is reacted with an alkyl metal compound of 1 to 12 carbon atoms per alkyl group whereby chain growth is produced and the carboxylic group is reduced to a carbonyl group, (f) the carbonyl group is reduced to form an alkyl group, and (g) a cyano group is introduced in the 4'-, the 4''- or the 4'''-position of the aromatic substituent whereby the desired trans-4-alkyl-cyanoarylcyclohexane having the Formula (I) above is produced;

an improvement in said steps (a) through (c) whereby a trans isomer of said aryl substituted cyclohexane-4-carboxylic acid alkyl ester having the Formula (IV) above substantially free from its cis isomer is produced for treatment in step (d) above, which improvement comprises the steps of (a) hydrogenating an arylcarboxylic acid having the Formula (II) above at a temperature below −20° C. with solvated electrons in the presence of a proton donor to produce a mixture of both the corresponding cis and trans isomers of aryl substituted cyclohexa-2,5-diene-4-carboxylic acid having the formula:

(III);

[structure: Ar—[Ar]ₙ—cyclohexadiene—COOH]

wherein n is the same as in Formula I above;

(b) esterifying the produced carboxylic acids having the Formula (III) with a lower alkanol whereby a mixture of the corresponding arylcyclohexadiene carboxylic acid alkyl ester isomers is produced, (c) hydrogenating the mixed alkyl ester isomers with molecular hydrogen in anhydrous lower alkanol in the presence of a Pd/activated carbon catalyst whereby a mixture of the corresponding cis and trans isomers of 1-aryl substituted cyclohexane-4-carboxylic acid esters is produced having the formula:

(IV);

[structure: Ar—[Ar]ₙ—cyclohexane(H)—COO-lower alkyl]

and (c') heating said mixture of the cis and trans isomers of the aryl substituted cyclohexane-4-carboxylic acid alkyl esters to its boiling point under reflux under anhydrous conditions under an inert gas in a lower alkanol in the presence of an alkali metal of the group consisting of sodium or potassium whereby the cis alkyl ester present in the isomeric mixture is isomerized to the trans alkyl ester, and recovering said stereo-specifically substantially pure trans isomer of the aryl substituted cyclohexane-4-carboxylic acid alkyl ester.

2. Process according to claim 1 wherein the hydrogenation in step (a) is conducted at about −70° C. using sodium or potassium in liquid ammonia as the source of solvated electrons and absolute ethanol as the proton donor.

3. Process according to claim 2 wherein the carboxylic acids are first esterified in step (b) with methanol and the resulting methyl esters are then transesterified with ethanol in step (c) whereby 1-aryl substituted cyclohexane-4-carboxylic acid ethyl esters are produced in step (c).

4. Process according to claim 3 wherein the alkali metal and the lower alkanol in step (c') are sodium and ethanol, respectively.

5. Process according to claim 2 wherein the arylcarboxylic acid in step (a) is biphenyl-4-carboxylic acid and the alkyl metal compound in step (e) is n-butyl lithium.

6. Process according to claim 1 wherein the transcyclohexane-4-carboxylic acid in step (e) is reacted at about −70° C. in absolutely anhydrous tetrahydrofuran with alkyllithium and the ketone group of the resulting alkylcyclohexyl ketone is reduced to a methylene group according to a Clemmensen or Wolff-Kishner reaction.

7. Process according to claim 1 wherein the aryl substituent is perhalogenated prior to its isomerization in step (c'), and is again completely dehalogenated subsequent to isomerization.

8. Process for the preparation of a stereospecifically substantially pure trans isomer of aryl cyclohexane-4-carboxylic acid alkyl ester useful in the production of a stereospecifically substantially pure trans-4-alkyl-cyanoarylcyclohexane having the formula:

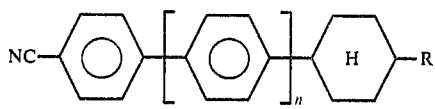

in which R is an unbranched or singly branched alkyl radical of 1 to 12 carbon atoms and n is an integer in the range from 0 to 2, which comprises (a) hydrogenating an arylcarboxylic acid of the formula:

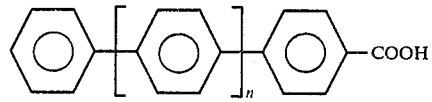

wherein n is the same as in Formula (I) above at a temperature below −20° C. by reaction with a solution of sodium or potassium in anhydrous liquid ammonia as a source for providing solvated electrons in the presence of absolute anhydrous ethanol as a proton donor whereby a mixture of both the corresponding cis and trans isomers of aryl substituted cyclohexa-2,5-diene-4-carboxylic acid is obtained having the formula:

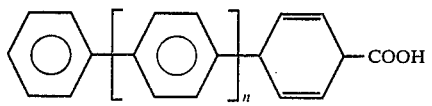

wherein n is the same as in Formula (I) above, and recovering said mixture of arylcyclohexadiene carboxylic acid isomers having the formula (III);

(b) esterifying said mixture of arylcyclohexadiene carboxylic acid isomers by reaction with a lower alkanol whereby a mixture of the corresponding arylcyclohexadiene carboxylic acid alkyl ester isomers is formed, (c) hydrogenating the mixed ester isomers with molecular hydrogen in anhydrous lower alkanol in the presence of a Pd/activated carbon catalyst whereby a mixture comprising the corresponding cis and trans isomers of 1-aryl substituted cyclohexane-4-carboxylic acid alkyl ester is formed having the formula:

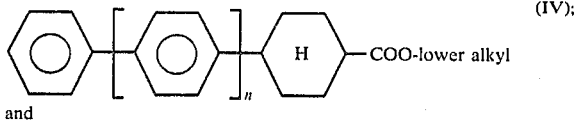

and (d) heating the mixture of said cis and trans isomers of the aryl substituted cyclohexane-4-carboxylic acid alkyl ester to its boiling point under reflux under anhydrous conditions under an inert gas in a lower alkanol in the presence of sodium or potassium whereby the cis ester present in the isomeric mixture is isomerized to the corresponding trans alkyl ester and a reaction mixture substantially free from said cis ester isomer is formed, and recovering substantially pure trans alkyl ester from said reaction mixture.

9. Process according to claim 8 wherein the hydrogenation in step (a) is conducted at about −70° C. using sodium in liquid ammonia as the source of solvated electrons.

10. Process according to claim 8 wherein the arylcarboxylic acid in step (a) is biphenyl-4-carboxylic acid, wherein said arylcyclohexadiene carboxylic acid isomers in step (b) are first esterified with methanol and then transesterified with ethanol before hydrogenating in step (c) of the resulting arylcyclohexadiene carboxylic acid alkyl ester isomers and isomerization in step (d) of the cis isomer in the isomer mixture of the arylcyclohexane carboxylic acid esters produced in step (c), and wherein the lower alkanol in both steps (c) and (d) is ethanol.

* * * * *